US00PP32127P2

(12) United States Plant Patent
Hansen

(10) Patent No.: US PP32,127 P2
(45) Date of Patent: Aug. 25, 2020

(54) ***HOSTA* PLANT NAMED 'SILLY STRING'**

(50) Latin Name: ***Hosta* hybrid (Tratt.)**
Varietal Denomination: Silly String

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/602,622

(22) Filed: Nov. 8, 2019

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
CPC ... A01H 5/12; A01H 5/02; A01H 5/00; A01H 6/12; A01H 6/56
See application file for complete search history.

*Primary Examiner* — June Hwu

(57) ABSTRACT

A new and distinct *Hosta* plant named 'Silly String' with small, rounded-mound habit of arching, glaucous, blue-green, long thin foliage. Leaves have slight fold and very wavy margins. The plant produces light purple flowers in mid-summer on nearly upright to slightly arching scapes well above the foliage.

2 Drawing Sheets

Latin name and variety denomination of the plant:
Botanical classification: *Hosta* hybrid (Tratt.).
Variety denomination: 'Silly String'.

STATEMENT REGARDING PRIOR DISCLOSURES UNDER 37 CFR 1.77(B)(6)

The non-enabling disclosure of the claimed plant, in the form of cultivar registration with The American *Hosta* Society which is the International Cultivar Registration Authority for the genus *Hosta* was by the inventor in December 2018 with public printing in early 2019. No plants of *Hosta* 'Silly String' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct *Hosta* plant, *Hosta* 'Silly String' hereinafter also referred to as the new plant or just the cultivar name, 'Silly String'. *Hosta* 'Silly String' the result of an intentional linear cross by the inventor on Aug. 22, 2013 at a wholesale nursery greenhouse in Zeeland, Mich., USA. The female parent is *Hosta* 'Curly Fries' (not patented) and the male parent is an unreleased proprietary hybrid known only by the breeder code H10-429-01 (not patented). The new plant passed initial evaluation in the summer of 2015, was give the breeder code 13-467-4 and was approved for final selection in the summer of 2016. The new plant has been asexually propagated by division at the same nursery in Zeeland, Mich., USA since 2016 and also by careful plant tissue culture with the resultant asexually propagated plants having retained all the same traits as the original plant. *Hosta* 'Silly String' is stable and reproduces true to type in successive generations of asexual reproduction in both methods.

BRIEF SUMMARY OF THE PLANT

There are nearly 6,000 registered *Hosta* cultivars with The American *Hosta* Society, which is the International Cultivar Registration Authority for the genus *Hosta* along with a similar number of unregistered cultivars. The nearest comparison varieties are 'Blue Cascade' (not patented) and 'Curly Fries'. 'Blue Cascade' has glaucous intensely wavy foliage, but the leaves are larger and broader and the habit is larger. 'Curly Fries' has chartreuse foliage that is less glaucous with less intense wavy margins. The male parent had glaucous-blue, heart-shaped leaves and larger habit.

Other similar *Hostas* include: 'Elvis Lives' (not patented), 'Little Wiggler' (not patented), 'Pineapple Poll' (not patented), 'Blue Sliver' (not patented) and 'Sugar Plum Fairy' (not patented). 'Elvis Lives' forms a larger clump and has a wider leaves. 'Little Wiggler' is smaller in habit and leaf size, the leaves are shiny and not glaucous and the flowers are lighter purple. 'Pineapple Poll' has thinner-substance, shorter and slightly broader leaf blades without glaucous surfaces with less intense sinuate margins. 'Blue Sliver' is a smaller plant with less undulation of the foliage. 'Sugar Plum Fairy' has a smaller habit and the foliage lacks the intense wavy margin and is shiny and not glaucous.

*Hosta* 'Silly String' is distinct from the above mentioned *Hostas* and all other cultivars known to the discoverer by the following combined traits:

1. Small rounded-mound plant habit with arching, glaucous, blue-green foliage;
2. Foliage is narrowly lanceolate to linear, slightly folded with very wavy margins;
3. Light purple flowers on tall nearly upright to slightly arching stapes.

BRIEF DESCRIPTION OF THE DRAWINGS

The photographs of the new plant demonstrate the overall appearance of a six-year-old plant, including the unique traits of 'Silly String'. The colors are as accurate as reasonably possible with color reproductions. Ambient light spectrum, temperature, source and direction may cause the appearance of minor variation in color.

DETAILED BOTANICAL DESCRIPTION

Figure 1:
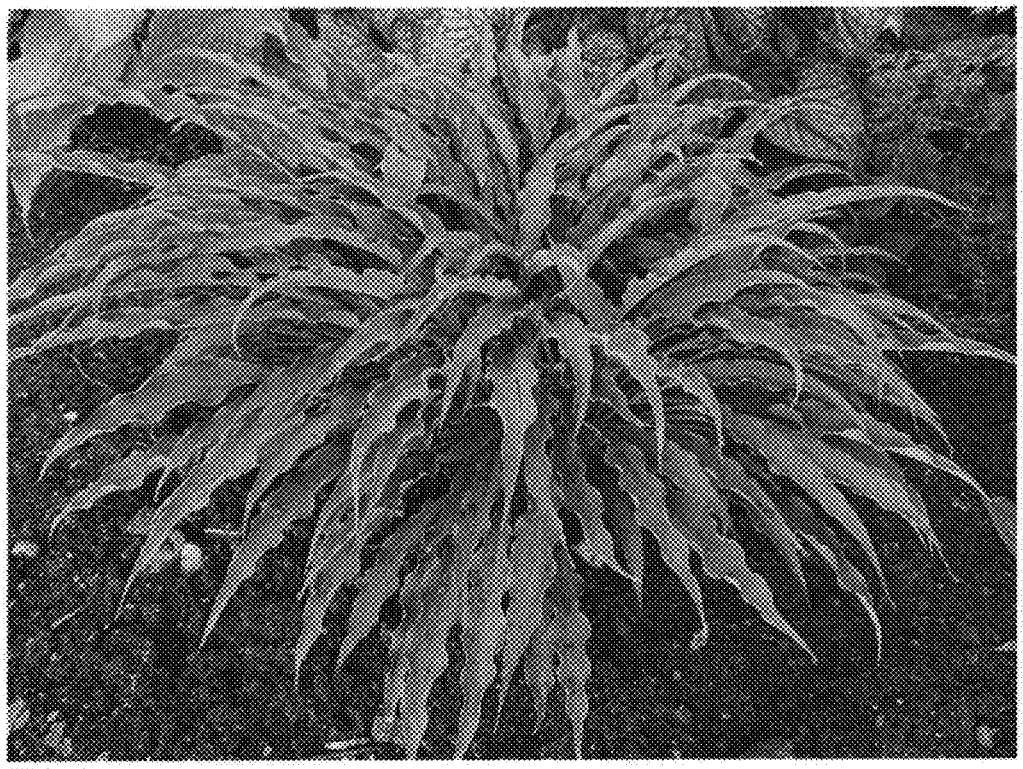
FIG. 1 shows a plant grown in a shaded trial garden with early summer foliage.
Figure 2:
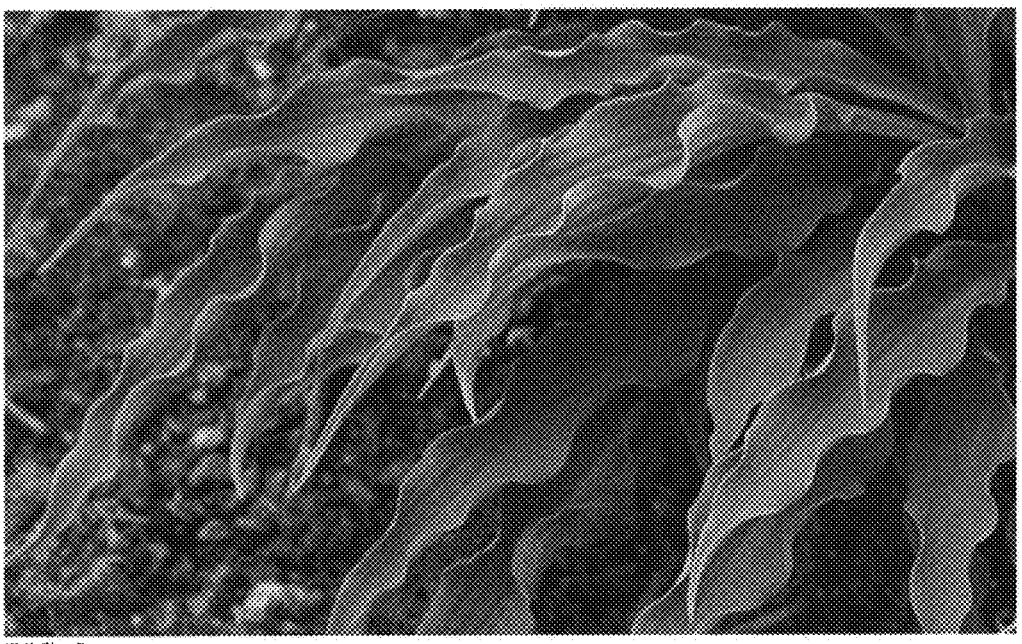
FIG. 2 shows a close-up of a leaf with the wavy margins in early summer.
Figure 3:
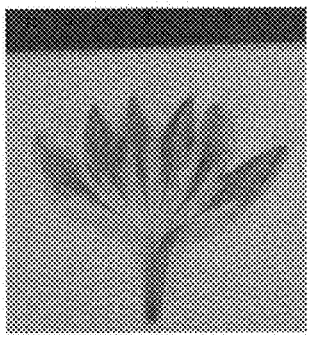
FIG. 3 shows the inside of a dissected flower.
Figure 4:
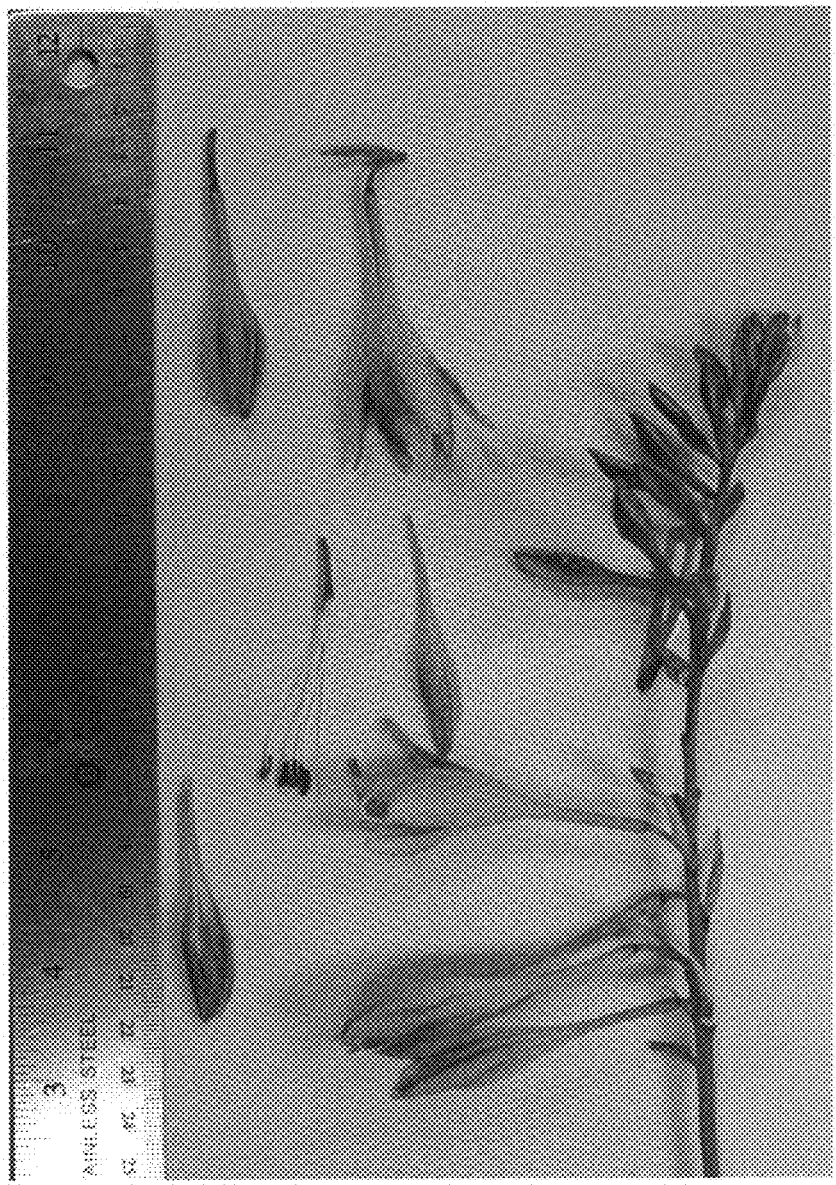
FIG. 4 shows a scape with excised bud, flower inside and outside, stamen and pistil.

The following descriptions and color references are based on the 2015 edition of The Royal Horticultural Society Colour Chart except where common dictionary terms are used. The new plant, *Hosta* 'Silly String', has not been observed under all possible environments. The phenotype may vary slightly with different environmental conditions, such as temperature, light, fertility, moisture and maturity levels, but without any change in the genotype. The following observations and size descriptions are of a six-year-old plant in a shaded trial garden in Zeeland, Mich. with supplemental water and fertilizer.

Botanical classification: *Hosta* hybrid;

Parentage: Female parent is 'Curly Fries'; male parent is known only by the breeder code H10-429-01 comprising 'Medusa' (not patented), 'Blue Cascade' (not patented) and proprietary unpatented selections of both *Hosta venusta* and *Hosta pulchella;*

Propagation: Garden division and sterile shoot-tip tissue culture;

Time to initiate roots from tissue culture: About two to three weeks;

Growth rate: Moderate;

Crop time: About 14 to 18 weeks to finish during the summer in a one-liter container from rooted tissue culture plantlet;

Rooting habit: Normal, fleshy, lightly branching;

Root color: Variable, nearest RHS 155D depending on soil type;

Plant shape and habit: Hardy herbaceous perennial with basal rosette of arching leaves emerging from rhizomes producing a large symmetrical rounded-mound of leaves;

Plant size: Foliage height to about 30.0 cm from the soil line to the top of the leaves and about 72.0 cm wide at the widest point slightly above the soil line;

Foliage description: Narrowly lanceolate to linear; glabrous, moderately glaucous adaxial and heavily glaucous abaxial; margin entire and sinuate; narrowly acute apex with attenuate base; with slight dimpling between veins;

Leaf blade size: To about 16.0 cm long and 24.0 mm wide and folded to about 8.0 mm deep toward base;

Leaf blade color: Early season and shortly after emerging adaxial between RHS 137A and RHS 137B, abaxial nearest RHS 137B; flowering season adaxial nearest RHS N138D, abaxial nearest blend between RHS N138D and RHS 189B and center nearest RHS 188C;

Petiole: Entire, glabrous, concavo-convex; slightly arching from base of plant to leaf base; to about 16.5 cm long and at base 4.0 mm across;

Petiole color: Adaxial and abaxial distally nearest RHS N138D, adaxial becoming maculate proximally with RHS 187B, maculate more densely abaxial with larger spots nearest RHS 187B;

Veins: Parallel; slightly impressed adaxial, slightly costate abaxial; 4 to 6 pairs with one midrib, average 5 pairs;

Veins color: Expanding adaxial and abaxial same as surrounding tissue; mature abaxial midrib and secondary nearest RHS 146D, mature abaxial midrib nearest RHS 145D and secondary nearest RHS 146D;

Flower description:

Buds one day prior to opening: Clavate with acute apex and narrow tubular base; about 48.0 mm long, apical bulb about 10.0 mm diameter and tube 22.0 mm long and about 2.0 mm diameter;

Bud color: Variable; nearest RHS N82D and RHS 86D, maculate near tepal margins with spots nearest RHS 86A, and apex nearest RHS 143A;

Flowers: Perfect; campanulate, funnelform with distally flaring tepals; actinomorphic; attitude drooping; about 28.0 mm wide and 70.0 mm long to exserted stigma, corolla portion 60.0 mm long and distally flared to 28.0 mm, fused tube portion about 22.0 mm long and 3.0 mm diameter (distal flowers smaller); persistent; effective for a normal period, typically one day on plant or as cut flower; stapes remain effective with flowers beginning early summer for about three weeks; about 26 flowers per scape; average spacing between flowers about 7.6 mm, significantly greater in proximal flowers;

Inflorescence: Flowering in upper 20.0 cm of peduncle and about 11.5 cm wide;

Flower period: Beginning late July and continuing for about five weeks to the end of August;

Floral bracts: Lanceolate; narrowly acute apex; truncate clasping base; concavo-convex; to about 17.0 mm long and 3.5 mm wide decreasing distally, average about 15.5 mm long and 3.0 mm across; dehiscing around individual flower anthesis period;

Floral bract color: Prior to flower anthesis adaxial and abaxial distally nearest RHS 146B and proximally nearest 77A;

Cauline bracts: Typically three below initial flowers; lanceolate; narrowly acute apex; truncate clasping base; concavo-convex; to about 20.0 mm long and 4.5 mm wide; color same as floral bracts;

Flower fragrance: None detected;

Tepal: Six; two sets of three, glabrous, entire; both sets lanceolate to spatulate; with acute apex; fused in basal 36.0 mm;

*Inner set*.—Not vitreous along margin; approximately 70.0 mm long and about 11.0 mm wide.

*Inner set color*.—Adaxial vitreous in distal 12.0 mm along fusion; nearest blend of RHS N82C and RHS 85A in distal 15.0 mm and into longitudinal center for 18.0 mm decreasing in width proximally, with slightly darker veins nearest RHS N88B and margins nearest RHS NN155D, corolla tube lighter than a blend between RHS 76B and RHS N82D; abaxial distally nearest blend between RHS N82D and RHS 85A and corolla tube nearest RHS N82C.

*Outer set*.—Vitreous along margin and in distal 12.0 mm along fusion; adaxial nearest blend between RHS N82C and RHS 85A in distal 15.0 mm and longitudinal center 18.0 mm decreasing in width proximally, with slightly darker veins nearest RHS N88B and adaxial corolla tube lighter than a blend between RHS 76B and RHS N82D; abaxial distally nearest blend between N82D and RHS 85A, corolla tube nearest RHS N82C.

Gynoecium: Single; tri-carpelled; 66.0 mm long;

*Style*.—Single; cylindrical; approximately 60.0 mm long, 0.8 mm diameter, curved upward about 180° in distal 12.0 mm; color between RHS NN155C and RHS NN155B in distal 10.0 mm and transitioning to nearest RHS 157D in proximal 5.0 mm.

*Stigma*.—Tri-lobed, about 1.0 mm tall and 1.5 mm across; color nearest RHS 11C.

*Ovary*.—Superior; ellipsoidal, lightly fluted longitudinally; about 5.0 mm long and 2.5 mm diameter at widest; acute apex and truncate base; color nearest RHS 145C.

Androecium: 6;

*Filaments*.—Cylindrical; approximately 58.0 mm long and 0.7 mm in diameter; curved around nearly 189° in the distal 12.0 mm; free except rarely adnate with inner corolla in proximal 1.0 mm; color nearest RHS NN155B distally and nearest RHS 145D proximally.

*Anthers*.—Elliptical; dorsifixed, longitudinally dehiscent; about 6.0 mm long and 2.5 mm wide and 1.0 mm thick; color nearest RHS N187A post-anthesis, prior to anthesis ventrally nearest RHS N77C and dorsally nearest RHS 177C.

*Pollen*.—Abundant; elliptic, less than 0.1 mm long; color nearest RHS 13A.

Peduncle: Cylindrical; usually one per mature division and twelve per plant; strongly glaucous, glabrous; nearly upright to slightly arching; to about 69.0 cm tall, and up to about 11.5 mm in diameter at base; average about 62.0 cm tall and about 12.0 mm diameter at base;

Peduncle color: Nearest RHS 146C heavily maculate with RHS N79A without glaucous bloom; with glaucous bloom nearest RHS N148C and maculate between RHS N77C and N187C;

Pedicel: Glabrous; glaucous; cylindrical; to 16.0 mm long and 1.0 mm diameter; attitude outwardly; color nearest RHS 86D with glaucous bloom and nearest RHS 79C with glaucous bloom removed;

Fruit: Tri-valved dehiscent capsule; elliptic; apiculate apex and rounded base; rugose; about 24.0 mm long and 4.5 mm diameter; color as maturing nearest RHS N187A, at maturity between RHS 199A and RHS N199A;

Seed: Typically about 21 per capsule; endospermic; flattened-elliptic wing surrounding embryo situated toward one end of ellipse; up to 11.0 mm long and 2.0 mm wide and 1.0 mm thick at embryo; color nearest RHS 202A;

Disease tolerance and resistance: *Hosta* 'Silly String' has not shown any resistance to pests and diseases common to *Hostas*. The plant grows best and shows best coloration with plenty of moisture, adequate drainage and light shade, but is able to tolerate some drought when mature. Hardiness at least from USDA zone 3 through 9, and other disease resistance is typical of that of other *Hostas*.

It is claimed:

1. A new and distinct ornamental plant cultivar named *Hosta* 'Silly String' as herein described and illustrated.

* * * * *